US009146195B2

(12) United States Patent
Spellicy

(10) Patent No.: US 9,146,195 B2
(45) Date of Patent: Sep. 29, 2015

(54) SYSTEMS AND METHODS FOR RADIANCE EFFICIENCY MEASUREMENT

(76) Inventor: Robert L. Spellicy, Round Rock, TX (US)

( * ) Notice: Subject to any disclaimer, the term of this patent is extended or adjusted under 35 U.S.C. 154(b) by 773 days.

(21) Appl. No.: 13/152,582

(22) Filed: Jun. 3, 2011

(65) Prior Publication Data

US 2011/0301910 A1 Dec. 8, 2011

Related U.S. Application Data

(60) Provisional application No. 61/351,555, filed on Jun. 4, 2010.

(51) Int. Cl.
| G06F 15/00 | (2006.01) |
| G01N 21/72 | (2006.01) |
| G01N 21/27 | (2006.01) |
| G01N 21/17 | (2006.01) |
| G01N 21/35 | (2014.01) |

(52) U.S. Cl.
CPC .............. *G01N 21/72* (2013.01); *G01N 21/274* (2013.01); *G01N 2021/1793* (2013.01); *G01N 2021/3595* (2013.01)

(58) Field of Classification Search
USPC ........................................................ 702/135
See application file for complete search history.

(56) References Cited

U.S. PATENT DOCUMENTS

| 6,295,859 | B1 * | 10/2001 | Hayden et al. ................. 73/23.2 |
| 7,491,944 | B1 * | 2/2009 | Stork et al. ............... 250/390.07 |
| 2003/0225532 | A1 * | 12/2003 | Stedman et al. ................. 702/24 |
| 2009/0257622 | A1 * | 10/2009 | Wolowelsky et al. ........ 382/103 |
| 2011/0195364 | A1 * | 8/2011 | Tullos ............................... 431/2 |
| 2011/0301910 | A1 * | 12/2011 | Spellicy ........................ 702/135 |

OTHER PUBLICATIONS

Sønnik Clausen Infrared low resolution emission spectroscopy of hot gases, Risø National Laboratory, Optics and Fluid Dynamics Department, P.O. Box 49, DK-4000 Roskilde, Denmark, Part of the SPIE Conference on Electro-Optical Technology for Remote Chemical Detection and Identification III , Orlando, Florida, Apr. 1998, pp. 133-139, SPIE 3383.*
URS Corporation, "Passive FTIR Phase I Testing of Simulated and Controlled Flare Systems," Jun. 2004, Houston and Austin, Texas, USA, 144 pages.
International Search Report and Written Opinion issued Feb. 9, 2012 in International Patent Application Serial No. PCT/US2011/039074.

* cited by examiner

*Primary Examiner* — Tung S Lau

(57) ABSTRACT

Radiance efficiency measurement. A non-transitory machine-readable storage medium includes executable instructions that, when executed, cause one or more processors to calculate, based on input radiation data, which is based on radiation from a radiation source, a difference of a radiance of the radiation source and a radiance of a background to the radiation source. The one or more processors are further caused to calculate, based on the difference, a transmissivity of the radiation source such that the calculated transmissivity of the radiation source is defined for flare combustion temperatures. The one or more processors are further caused to output the transmissivity of the radiation source.

14 Claims, 3 Drawing Sheets

SYSTEMS AND METHODS FOR RADIANCE EFFICIENCY MEASUREMENT

CROSS REFERENCE TO RELATED APPLICATION

This application claims priority to U.S. Provisional Application Ser. No. 61/351,555 titled "Radiance Efficiency Measurement," filed Jun. 4, 2010, incorporated herein by reference.

BACKGROUND

Emission, combustion, and efficiency estimates for flares are in need of improvement. Current estimates are based on factors gleaned from limited data, and environmental factors during flare operation are rarely taken into account. Extractive sampling methods generally collect an aliquot of the pollutant gases or species of interest from within a well-mixed exhaust stack prior to release into the atmosphere. In most cases, these exhaust stacks are equipped with platforms and sampling ports to permit easy access for the sampling equipment and personnel. As such, a variety of continuous or integrated measurement techniques can be used to quantify the emissions from these sources. Because the combustion of flares occurs at the flare tip, and the exhaust gases are emitted directly to the atmosphere at a height of several hundred feet, use of stack sampling methods for characterizing flare emissions are not practical.

DETAILED DESCRIPTION OF THE INVENTION

Figure 1:
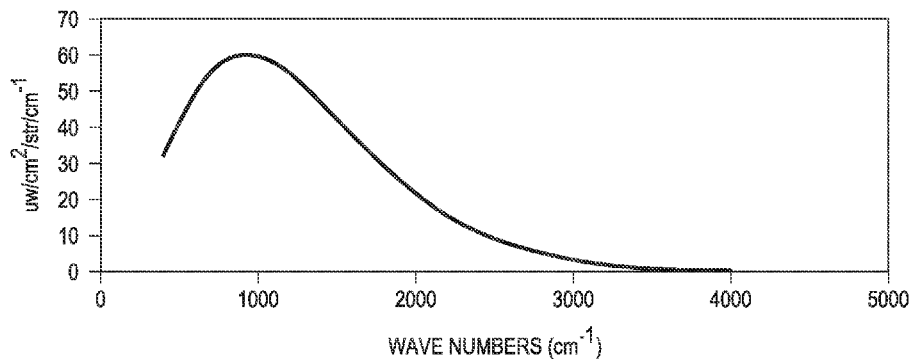
FIG. 1 illustrates a Planck function in accordance with at least some illustrative embodiments.

Considering the above, it is desirable to be able to determine flare combustion efficiency during operation. In absorption spectroscopy, light is passed through a region containing gas to be analyzed, and the transmitted light is spread out into a spectrum using an interferometer or a spectrometer. The presence of specific compounds can be determined from the patterns of light absorbed while the compound's concentrations can be measured from the intensity of the patterns. The low energy of infrared light is absorbed by molecular species causing the molecules to vibrate and rotate faster. Because each molecule consists of a unique structure of bound atoms, the patterns of infrared wavelengths (IR colors) absorbed by a molecule are also unique. These molecular patterns can be analyzed to measure emissions in the plume of the flare. "Flare" and "plume" are used interchangeably in this disclosure.

"Active" measurement techniques measure flares by transmitting a collimated beam of infrared light through a plume and positioning a detector on the opposite side of the plume. Alternatively, a retro-reflecting mirror may be placed on the opposite side, thus returning the beam to the Active Fourier Transform Infrared (AFTIR) system. As such, the AFTIR equipment detects the amount of energy absorbed by those compounds of interest. The specific wavelengths absorbed are indicative of the presence of specific compounds being present, and the amount of light that is absorbed is proportional to the concentration of these compounds. However, the plume may change its direction of travel (relative to the light source) because of prevailing winds, thus requiring periodic re-alignment of the active light source and detector.

Unlike spectroscopic methods that rely on detecting the amount of light that is absorbed to identify and quantify the compounds, or specie(s), present, Passive Fourier Transform Infrared (PFTIR) operates on the principle of analyzing the amount of thermal radiation emitted by hot gases. The technique is "passive" because no active infrared light source is used. Rather, the hot gases of the flare become the infrared (IR) source, and PFTIR is used to measure the amount of energy radiated from the plume. The use of PFTIR is possible because the IR radiation emitted by hot gases has the same pattern of wavelengths as the corresponding infrared absorption spectra. Consequently, observing a flare from a distance with an IR instrument coupled to a receiver telescope allows for the rapid identification and quantification of the species in the plume. A receiver telescope may be an optical remote sensing device that can measure properties of a target by illuminating the target with light, such as a laser. In this case, the signature arising from the hot gases is proportional to the concentration of the gas and to its temperature. Therefore to conduct PFTIR measurements, the temperature is calculated from the measured radiation data. The PFTIR can be calibrated in absolute units of radiance (watts/cm2/ster/cm-1) using a black body radiation source.

PFTIR is ideal for sampling flares for multiple reasons. First, passive remote sensing using PFTIR measures flare emissions non-intrusively and at a distance, thus eliminating the need for special cones, sampling rakes, and lifting devices to hoist sampling packages into position over the plume. Such actions are labor intensive and logistically complicated. Second, PFTIR is cost effective. PFTIR can measure many compounds simultaneously (many of which are products of complete and incomplete combustion), thus eliminating the need for multiple measurements. Finally, PFTIR directly assesses flare performance continuously and in real-time. Such assessment is advantageous when measuring flares that may be over-steamed (or air-assisted), when characterizing the effects of wind speed on flare efficiency, and when unique environmental factors must be taken into consideration.

Combustion efficiency can be calculated based on the following equation:

$$Eff = \frac{[CO_2]}{[CO_2] + [CO] + [THC] + [soot]} \quad (1)$$

where $[CO_2]$ is the carbon dioxide ($CO_2$) concentration, $[CO]$ the carbon monoxide (CO) concentration, $[THC]$ the concentration of total hydrocarbons in the gas phase, and $[soot]$ is the concentration of any soot present (i.e. the amount of hydrocarbon particulate matter). Knowledge of the flare's input gas composition will be helpful.

The PFTIR instrument is calibrated utilizing a light source of known spectral radiance. The radiance calibration of a PFTIR instrument relates the output voltage of the instrument to the received energy in radiance units. Radiance is given by watts per square centimeter of source area, per unit solid angle of observation, and per unit wavelength or wave number of detection (watts/cm2/steradian/wave number). An infrared black body source can be used for calibration. The Planck radiation law gives the power emitted by a perfect black body as a function of temperature, T, and wave number, v. This function is given by:

$$N_{BB}(v, T) = \frac{2hv^2 v^3}{e^{hcv/kT} - 1} \quad (2)$$

Here, h is Planck's constant, c is the speed of light, and k is the Boltzmann constant. This function is plotted in FIG. 1 for a temperature of 200° C. Hotter objects will emit shorter wavelengths (in the visible ranges) while cooler bodies emit longer wavelengths (in the IR ranges). Accordingly as temperature rises, the peak of this function moves to the right along the x-axis toward larger wave numbers (smaller wavelength). If a body is not "black" (e.g. totally absorbing), the energy it emits is the Planck function multiplied by the body's transmissivity. Gases have absorption that is variable with wavelength, and this variation produces the absorption patterns that allow for the identification of gases in IR. If the transmissivity of a gas is given by $\tau$ (v,T), then [1−$\tau$ (v,T)] is the amount of absorption. The radiation emitted by gas at temperature T and wave number v is given by:

$$N(v,T) = [1 - \tau(v,T)] * N_{bb}(v,T) \quad (3)$$

Figure 2:
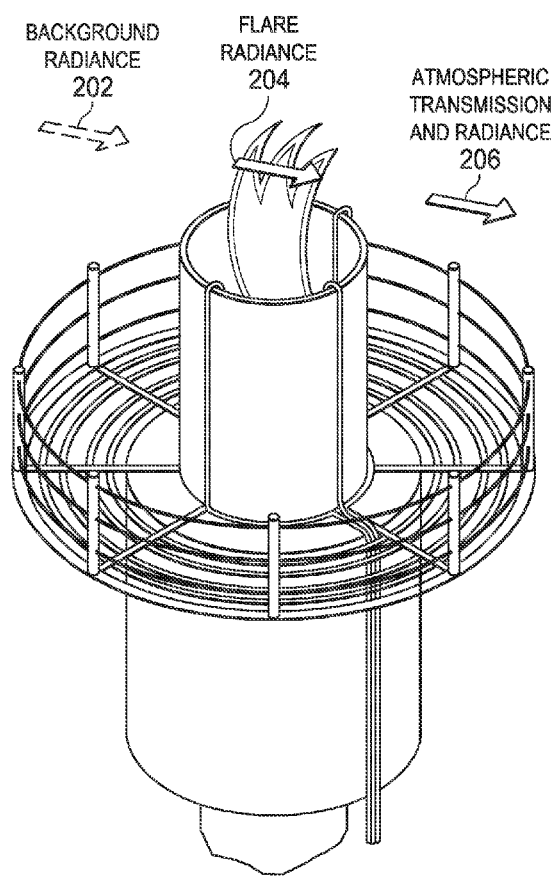
FIG. 2 illustrates contributions to the measured radiance in accordance with at least some illustrative embodiments

However in addition to flare radiance, other contributions make up the signal that the PFTIR system detects in the field. As shown in FIG. 2, the background (for example, the sky) has some IR emission, which is labeled background radiance 202. As discussed, the flare radiance 204 is also transmitted. Finally, the atmosphere between the flare and the PFTIR also has its own IR emissions labeled atmospheric radiance 206. Thus, the total radiation data received consists of:

$$N_{total} = N_{bkg} * \tau_{flr} * \tau_{atm} + N_{flr} * \tau_{atm} + N_{atm} + N_f \quad (4)$$

In this equation, $N_{total}$ is total radiance, $N_{bkg}$ is background radiance, $\tau_{flr}$ is flare gas transmissivity, $\tau_{atm}$ is atmospheric transmissivity, $N_{flr}$ is flare radiance, $N_{atm}$ is atmospheric radiance, and Nf is the radiance of the PFTIR equipment itself.

Measurements performed by the PFTIR system and calculations performed by a processor coupled to the system consist of the following: $M_{flr}$ is the calculated flare radiance, and $M_b$ is the measured background radiance taken by moving the PFTIR off the flare to monitor the sky background. $M_b$ is given by $$M_b = N_{bkg} * \tau_{atm} + N_{atm} + N_f \quad (5)$$

$M_n$ is the measurement made pointing the PFTIR system at the calibration source with a cold (e.g., liquid nitrogen) emitter in place, $M_{bb}$ is the measurement made pointing the PFTIR system at the calibration source with a black body emitter in place, and $T_{atm}$, is the calculated atmospheric transmissivity. Based on these measurements, Equation (3) can be rearranged to give the flare transmissivity as:

$$\tau_{flr} = \frac{C * (M_{flr} - M_n) - N_{BB}^{flr} * \tau_{atm}}{C * (M_b - M_n) - N_{BB}^{flr} * \tau_{atm}} \quad (6)$$

In Equation (6), the superscript "flr" on the Planck function ($N_{BB}$) denotes that this is the Planck function calculated at the temperature of the flare. C is the calibration measurement made with a black body calibration source. This factor converts the FTIR voltages to radiance units, and it is given by:

$$C = \frac{N_{BB}^{BB}}{(M_{bb} - M_n)} \quad (7)$$

The measured black body radiance ($M_{bb}$) has the cold source measurement ($M_n$) subtracted to cancel emissions from the intervening air and/or the PFTIR instrument itself. Atmospheric transmissivity $\tau_{atm}$ is also measured using the calibration source. In at least one embodiment, the black body is replaced by a standard infrared source, and the measurement is made at a path length roughly equal to that of the path from the PFTIR to the flare. Atmospheric transmissivity is then given by:

$$\tau_{atm} = \frac{M_{IR} - M_n}{I_0} \quad (8)$$

$M_{IR}$ is the measured signal from the calibration source using the IR source, and $M_n$ is the measured cold source as defined earlier. $I_0$ is the so-called synthetic background. It represents the shape of the spectrum that the PFTIR would measure if no gases were present. In at least one embodiment, it is calculated from the ($M_{IR}-M_n$) measurement by doing a mathematical fit to points in the spectrum known to be free of molecular absorptions. With equations (7) and (8), equation (6) then contains only measured or calculated terms.

Figure 3:
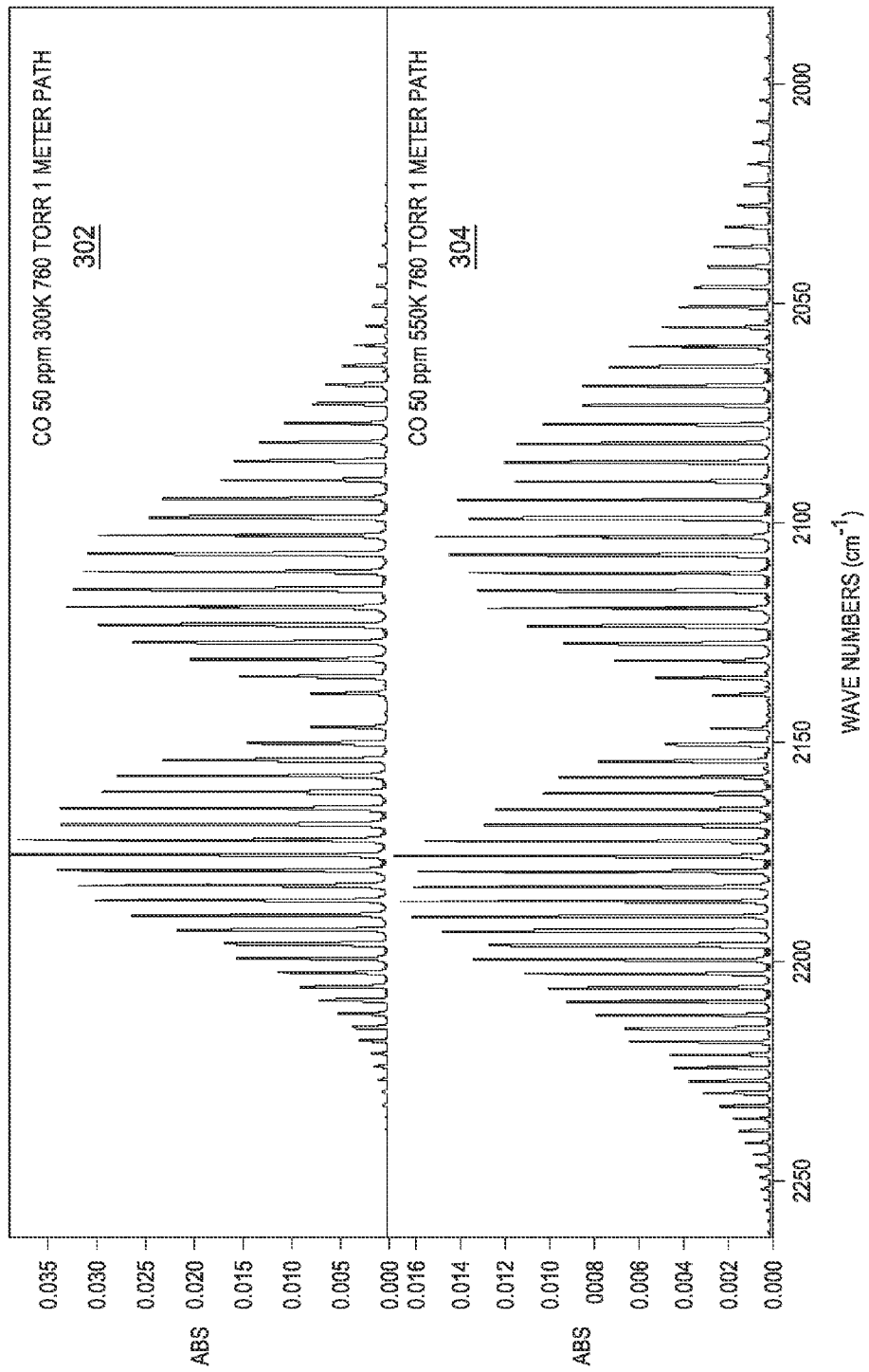
FIG. 3 illustrates alteration of band shape in accordance with at least some illustrative embodiments.

However, to calculate the Planck function at the temperature of the flare, the flare gas temperature must be known. In at least one embodiment, the temperature is calculated based on spectral analysis of carbon monoxide or carbon dioxide in the flare. FIG. 3 illustrates the CO band near 2150 cm$^{-1}$ at two different temperatures. The upper plot 302 is at ambient temperature (300 K), and the bottom plot 304 is at 550 K. As can be seen, the effect of increasing temperature is to expand the band shifting the peak amplitude positions away from band center while increasing the amplitude of the weaker peaks farther from band center. Because these measurements are sensitive to temperature variations, the shape of the band is an accurate gauge for temperature.

The CO peaks represent a transition of the molecule from a higher vibration/rotation state to a lower one. The transitions are dictated by quantum mechanics. However, the intensities of the individual peaks are strongly influenced by the number of molecules in the initial state available to make the transition. This "population" of the initial states is dictated by the Boltzmann distribution which is given by:

$$N_{j''} = N_0 \frac{2J'' + 1}{Q} \exp\left[\frac{-E''}{kT}\right] \quad (9)$$

Here, $N_{j''}$ is the number of molecules in the initial rotational state defined by the rotational quantum number J". $N_0$ is the total number of molecules available, E" is the energy of the initial state, k is the Boltzmann constant, T is the absolute temperature, and Q is a partition sum. The partition sum is the sum of the exponential term over all possible energy levels. If the log of the measured intensity of the CO peaks is plotted against the initial state energy, the plot is linear, and its slope is proportional to $$\frac{hc}{kT},$$

where h is Planck's constant, and c is the speed of light. Temperature can therefore be determined by measuring the slope of the plot.

Given temperature, all terms in Equation (6) can be calculated. The transmissivity of the flare is given by:

$$\tau_{flr} = e^{-K(v)*c*l} \tag{10}$$

Where $K(v)$ is the absorption coefficient for the spectral line, c is the gas concentration, and l is the path length in the gas. Taking the negative log of this equation gives absorbance:

$$\text{Absorbance}(v) = K(v)*c*l \tag{11}$$

To calculate combustion efficiency, the concentrations of CO, $CO_2$, and Total Hydrocarbon (THC) are used in Equation (1):

$$\mathit{Eff} = \frac{[CO2]}{[CO2]+[CO]+[THC]+[\text{soot}]} \tag{1}$$

The remaining term, [soot], is the concentration of any soot present. If it is present at any significant concentration, it will be seen in the IR spectra as an attenuation of the signal with characteristic spectral shapes driven by particle size distribution.

Flare transmissivity can be defined for the range of flare combustion temperatures by avoiding division by terms that go to zero and by grouping like magnitude terms together. Using $$N_{flr} = (1-\tau_{flr})*L_{bb}^{flr} \tag{12}$$

the total measured plume radiance $M_{flr}$ as given above can then be written as:

$$M_{flr} = N_{flr}\tau_{atm} + N_{bkg}\tau_{atm}[1-N_{flr}/L_{bb}^{flr}] + N_{atm} + N_f \tag{13}$$

But from above, $$M_b = N_{bkg}*\tau_{atm} + N_{atm} + N_f \tag{14}$$

Rearranging the terms:

$$N_{flr} = \frac{(M_p - M_b)C}{\tau_{atm}\left(1 - \frac{N_{bkg}}{L_{bb}^{flr}}\right)} \tag{15}$$

But, $$N_{bkg} = \frac{(M_b - M_n)C}{\tau_{atm}} \tag{16}$$

Therefore, $$N_{flr} = \frac{(M_p - M_b)C}{\left[\tau_{atm} - \frac{(M_b - M_n)C}{L_{bb}^{flr}}\right]} \tag{17}$$

The denominator of Equation (17) is almost 1.0 in all analysis regions for the relevant temperatures and is a correction factor for the numerator. As such, $$Corr = \left[\tau_{atm} - \frac{(M_b - M_n)C}{L_{bb}^{flr}}\right] \tag{18}$$

Then, the flare radiance is given by:

$$N_{flr} = \frac{(M_p - M_b)C}{Corr} \tag{19}$$

And because $$N_{flr} = (1-\tau_{flr})*L_{bb}^{flr} \tag{20}$$

then $$\tau_{flr} = [1 - N_{flr}/L_{bb}^{flr}] \tag{21}$$

Using flare transmissivity with this correction factor generates a stable spectrum for the range of flare combustion temperatures.

Figure 4:
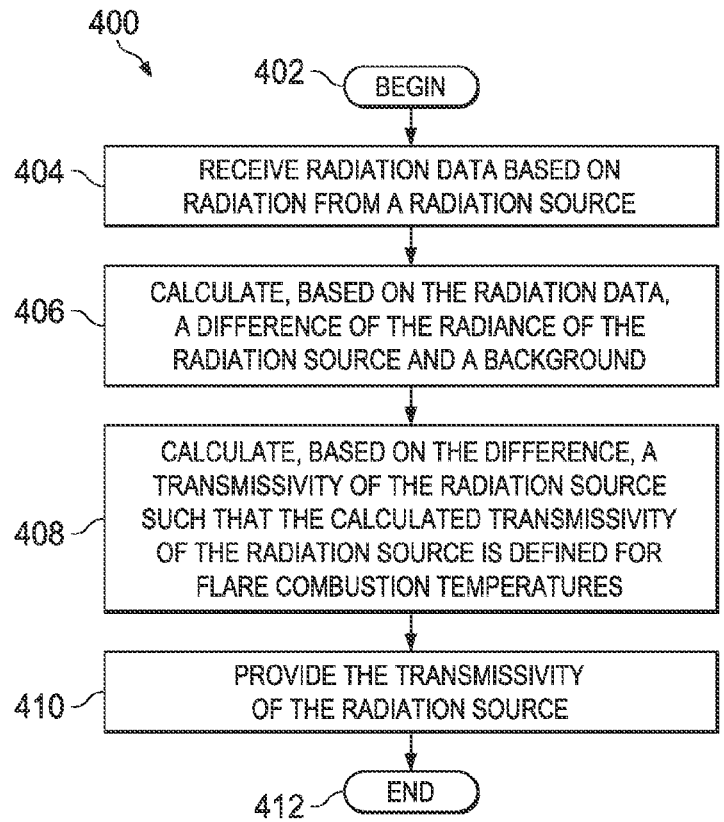
FIG. 4 illustrates a method of measuring radiance efficiency in accordance with at least some illustrated embodiments.

FIG. 4 illustrates a method 400 of radiance measurement beginning at 402 and ending at 412. The method 400 may include any action or calculation described in this disclosure. At 404, radiation data is received based on radiation from a radiation source. At 406, a correction factor based on atmospheric transmissivity is calculated based on the radiation data. In at least one embodiment, calculating the transmissivity of the radiation source comprises calculating, based on the correction factor, the transmissivity of the radiation source such that a calculated radiance of the radiation source is defined for the temperatures. In at least one embodiment, the correction factor is used to correct the calibrated difference between the measured radiance from the radiation source and the measured background radiance. The correction factor is approximately 1.0 for the temperatures in at least one embodiment. At 408, a transmissivity of the radiation source is calculated based on the correction factor such that the calculated transmissivity of the radiation source is defined for flare combustion temperatures. In at least one embodiment, the temperature of combustion is calculated based on spectral analysis of carbon monoxide in the radiation source. In an alternative embodiment, the temperature is calculated based on spectral analysis of carbon dioxide in the radiation source. At 410, the transmissivity of the radiation source is provided.

From the description provided herein, those skilled in the art are readily able to combine software created as described with appropriate computer hardware to create a special purpose computer system and/or special purpose computer sub-components in accordance with the various embodiments, to create a special purpose computer system and/or computer sub-components for carrying out the methods of the various embodiments and/or to create a computer-readable media that stores a software program to implement the method aspects of the various embodiments.

Figure 5:
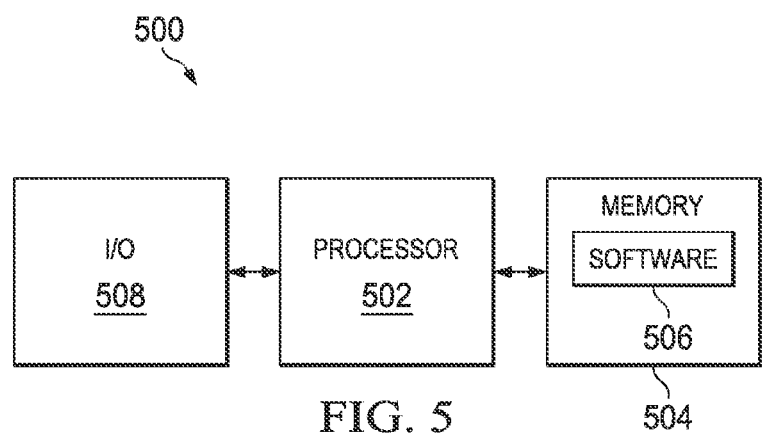
FIG. 5 illustrates radiance efficiency measurement tied to particular machine in accordance with at lest some illustrative embodiments.

FIG. 5 illustrates a computer system 500 in accordance with at least some embodiments, and upon which at least some of the various embodiments may be implemented. That is, some or all of the various embodiments may execute on a computer system such as shown in FIG. 5, multiple computers systems, and/or one or more computer systems equivalent to the FIG. 5 (such as scaled down computer systems for implementation in or within the onboard device), including after-developed computer systems.

In particular, the computer system 500 comprises a processor 502, and the processor couples to a main memory 504 by way of a bridge device. In some embodiments, the bridge device may be integrated with the processor 502. Moreover, the processor 502 may couple to a long term storage device (e.g., a hard drive) by way of the bridge device. Programs 506 executable by the processor 502 may be stored on the storage device, and accessed when needed by the processor 502. The programs 506 stored on the storage device may comprise programs to implement the various embodiments of the present specification, including programs to calculate retrieve rules, retrieve data, and implement and command radiance efficiency measurement, including receiving input and displaying output via peripheral devices 508. In some cases, the programs 506 are copied from the storage device to the main memory 504, and the programs are executed from the main memory 504. Thus, both the main memory 504 and storage device are considered machine-readable storage mediums.

In the specification, certain components may be described in terms of algorithms and/or steps performed by a software application that may be provided on a non-transitory machine-readable storage medium (i.e., other than a carrier wave or a signal propagating along a conductor). In many cases, such descriptions are intended to set forth the embodiments using representations that are used among those of skill in the arts. Accordingly, any descriptions that refer to algorithms, method steps, functional components, and the like, shall be considered to encompass electrical, magnetic, optical, and/or mechanical signals representing such algorithms, method steps, functional components, such signals being capable of being stored, input, output, and/or otherwise manipulated.

All such terms, and any similar terms, are to be considered labels only, and are intended to encompass any appropriate physical quantities or other physical manifestations. Any particular naming or labeling of the various modules, protocols, features, and the like is intended to be illustrative; other names and labels can be equivalently used. In addition, various terms such as "processing", "calculating", "determining", "transmitting", or the like, may be used herein. Such terms are intended to refer to processes performed by a software and/or hardware device such as a computer system. Such terms refer to various types of manipulation and/or transformation of physical and/or electronic components such as registers and memories within the device. These physical and/or electronic components typically represent data elements to be transformed, transmitted, and/or output.

Furthermore, the various aspects can be implemented as a method, system, computer program product, user interface, or any combination thereof.

The various embodiments also relate to a system for performing various steps and operations as described herein. This system may be a specially-constructed device such as an electronic device, or it may include one or more particular machines that can follow software instructions to perform the steps described herein. Multiple computers can be networked to perform such functions. Software instructions may be stored in any computer readable storage medium, such as for example, magnetic or optical disks, cards, memory, and the like.

The method steps, user interface layouts, displays, and other components described herein can be implemented on any computer, network, or other apparatus capable of performing the functions described. No limitation as to operation on a particular type of system or apparatus is implied. No particular programming language is required; rather, any type of programming language can be used to implement the various embodiments.

References to "one embodiment", "an embodiment", "a particular embodiment" indicate that a particular element or characteristic is included in at least one embodiment of the invention. Although the phrases "in one embodiment", "an embodiment", and "a particular embodiment" may appear in various places, these do not necessarily refer to the same embodiment.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A non-transitory machine-readable storage medium comprising executable instructions that, when executed, cause one or more processors to:
   calculate, based on input radiation data, which is based on measured radiation from a hot gas radiation source, a difference of the radiance from the hot gas radiation source and a measured background radiance;
   calculate, based on the difference, a transmissivity of the hot gas radiation source such that the calculated transmissivity of the radiation source is defined for flare combustion temperatures;
   output the transmissivity of the radiation source; and
   calculate a correction factor based on atmospheric transmissivity, wherein calculating the transmissivity of the hot gas radiation source comprises calculating, based on the correction factor, the transmissivity of the hot gas radiation source.

2. The medium of claim 1, wherein the one or more processors are further caused to calculate a temperature based on spectral analysis of carbon monoxide in the hot gas radiation source.

3. The medium of claim 1, wherein the one or more processors are further caused to calculate a temperature based on spectral analysis of carbon dioxide in the hot gas radiation source.

4. The medium of claim 1, wherein the one or more processors are caused to calculate, based on the correction factor, the transmissivity of the hot gas radiation source such that a calculated radiance of the hot gas radiation source is defined for the temperatures.

5. The medium of claim 1, wherein the hot gas radiation source is a flare.

6. A method, comprising:
   measuring radiation data based on radiation from a hot gas radiation source and a background radiance;
   calculating, by a processing unit, based on the radiation data, a difference of a measured radiance of the hot gas radiation source and a measured background radiance;
   calculating, by a processing unit, based on the difference, a transmissivity of the hot gas radiation source such that the calculated transmissivity of the hot gas radiation source is defined for flare combustion temperatures;
   providing the transmissivity of the hot gas radiation source; and
   calculating, based on the radiation data, a correction factor based on atmospheric transmissivity;
   wherein calculating the transmissivity of the hot gas radiation source comprises calculating, based on the correction factor, the transmissivity of the hot gas radiation source.

7. The method of claim 6, further comprising calculating a temperature based on spectral analysis of carbon monoxide in the hot gas radiation source.

8. The method of claim 6, further comprising calculating a temperature based on spectral analysis of carbon dioxide in the hot gas radiation source.

9. The method of claim 6, wherein calculating the transmissivity of the radiation source comprises calculating, based on the correction factor, the transmissivity of the hot gas radiation source such that a calculated radiance of the hot gas radiation source is defined for the temperatures.

10. The method of claim 6, wherein the hot gas radiation source is a flare.

11. A system, comprising:
one or more processors;
memory coupled to the one or more processors, the memory storing executable instructions that when executed by the one or more processors, cause the one or more processors to:
calculate, based on input radiation data in the memory a difference of a radiance of a hot gas radiation source and a background radiance, the radiation data based on measured radiation from the hot gas radiation source;
calculate, based on the difference, a transmissivity of the hot gas radiation source such that the calculated transmissivity of the hot gas radiation source is defined for flare combustion temperatures;
output the transmissivity of the hot gas radiation source; and
calculate a correction factor based on atmospheric transmissivity, wherein calculating the transmissivity of the hot gas radiation source comprises calculating, based on the correction factor, the transmissivity of the hot gas radiation source.

12. The system of claim 11, the one or more processors further caused to calculate a temperature based on spectral analysis of carbon monoxide in the hot gas radiation source.

13. The system of claim 11, the one or more processors further caused to calculate a temperature based on spectral analysis of carbon dioxide in the hot gas radiation source.

14. The system of claim 11, wherein the one or more processors are further caused to calculate, based on the correction factor, the transmissivity of the hot gas radiation source such that a calculated radiance of the hot gas radiation source is defined for the temperatures.

* * * * *